(12) United States Patent
Gallant et al.

(10) Patent No.: US 7,865,982 B2
(45) Date of Patent: Jan. 11, 2011

(54) HOSPITAL BED SIDE RAIL WITH MEDICAL TREATMENT CONTROL UNIT

(75) Inventors: Dennis J. Gallant, Harrison, OH (US); Dennis M. Lanci, Carlsbad, CA (US); Carl W. Riley, Milan, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 1797 days.

(21) Appl. No.: 11/005,583

(22) Filed: Dec. 6, 2004

(65) Prior Publication Data

US 2005/0102912 A1 May 19, 2005

Related U.S. Application Data

(62) Division of application No. 10/154,312, filed on May 23, 2002, now Pat. No. 6,895,715.

(60) Provisional application No. 60/293,949, filed on May 25, 2001.

(51) Int. Cl.
*A47C 21/08* (2006.01)

(52) U.S. Cl. .................................. 5/430; 5/428; 5/425

(58) Field of Classification Search ............. 5/425–430, 5/606, 621, 658, 662
See application file for complete search history.

(56) References Cited

U.S. PATENT DOCUMENTS

| 2,739,785 A | 3/1956 | Gray |
| 2,834,030 A | 5/1958 | Jones |
| 2,894,794 A | 7/1959 | Mays |
| 3,241,850 A | 3/1966 | Propst |
| 3,250,583 A | 5/1966 | Phillips |
| 3,267,955 A | 8/1966 | Logan et al. |
| 3,362,704 A | 1/1968 | Pilz |
| 3,462,920 A | 8/1969 | Denny |
| 3,514,794 A | 6/1970 | Pofferi |
| 3,567,842 A | 3/1971 | Meyer |
| 3,694,830 A | 10/1972 | Koller |
| 3,829,906 A | 8/1974 | McPhee |

(Continued)

FOREIGN PATENT DOCUMENTS

DE 570079 2/1933

(Continued)

OTHER PUBLICATIONS

Hill-Rom Company, Inc. Video 1 (Oct. 1998).

(Continued)

*Primary Examiner*—Michael Trettel
*Assistant Examiner*—William Kelleher
(74) *Attorney, Agent, or Firm*—Barnes & Thornburg LLP

(57) ABSTRACT

A headwall is adapted for use with a bed in a room of a healthcare facility. The headwall comprises a service delivery unit movable relative to a wall of the room between a storage position and a use position allowing the bed to dock to the service delivery unit to receive one or more services from the service delivery unit. It is disclosed to use the headwall to provide services to patient care equipment mounted to a side rail of the bed. Such patient care equipment is, for example, a chest drainage unit, an infusion unit, or a vacuum bandage unit.

15 Claims, 7 Drawing Sheets

U.S. PATENT DOCUMENTS

| | | | |
|---|---|---|---|
| 3,846,853 A | 11/1974 | Jacobsson | |
| 3,921,345 A | 11/1975 | Damico | |
| 4,072,157 A | 2/1978 | Wines, Jr. et al. | |
| 4,104,710 A | 8/1978 | Damico et al. | |
| 4,129,122 A | 12/1978 | Dout et al. | |
| 4,155,609 A | 5/1979 | Skafte et al. | |
| D253,246 S | 10/1979 | O'Toole | |
| 4,314,735 A | 2/1982 | Fullenkamp et al. | |
| 4,338,485 A | 7/1982 | Fullenkamp et al. | |
| 4,435,171 A | 3/1984 | Goldberg et al. | |
| 4,475,322 A | 10/1984 | Russo et al. | |
| 4,612,679 A | 9/1986 | Mitchell | |
| 4,646,211 A | 2/1987 | Gallant et al. | |
| 4,753,055 A | 6/1988 | Durham, Jr. | |
| 4,757,810 A | 7/1988 | Reese | |
| 4,768,241 A * | 9/1988 | Beney | 5/600 |
| 4,821,470 A | 4/1989 | Kappers et al. | |
| D302,502 S | 8/1989 | Durham, Jr. | |
| D303,743 S | 10/1989 | Durham, Jr. | |
| D303,889 S | 10/1989 | Durham, Jr. | |
| 4,905,433 A | 3/1990 | Miller | |
| 5,060,425 A | 10/1991 | Kappers et al. | |
| 5,097,550 A | 3/1992 | Marra, Jr. | |
| 5,107,636 A | 4/1992 | Schindele et al. | |
| 5,108,063 A | 4/1992 | Koerber, Sr. et al. | |
| 5,174,285 A | 12/1992 | Fontenot | |
| 5,247,962 A | 9/1993 | Walker | |
| 5,304,213 A | 4/1994 | Berke et al. | |
| 5,314,243 A | 5/1994 | McDonald et al. | |
| 5,319,816 A | 6/1994 | Ruehl | |
| 5,323,565 A | 6/1994 | Kappers et al. | |
| 5,337,845 A | 8/1994 | Foster et al. | |
| 5,382,244 A | 1/1995 | Telang | |
| 5,396,673 A | 3/1995 | Foster | |
| 5,448,859 A | 9/1995 | Walker et al. | |
| 5,455,975 A | 10/1995 | Foster | |
| 5,479,958 A | 1/1996 | Kummerfeld | |
| 5,507,734 A | 4/1996 | Everett, Jr. et al. | |
| 5,513,574 A | 5/1996 | Collins | |
| 5,542,136 A * | 8/1996 | Tappel | 5/710 |
| 5,555,582 A | 9/1996 | Jerideau | |
| 5,588,167 A * | 12/1996 | Pahno et al. | 5/606 |
| 5,623,948 A | 4/1997 | VanMorris | |
| 5,653,064 A | 8/1997 | Kappers et al. | |
| 5,732,423 A * | 3/1998 | Weismiller et al. | 5/425 |
| 5,756,933 A | 5/1998 | Pitchford et al. | |
| 5,800,189 A | 9/1998 | Ahmed | |
| 5,831,802 A | 11/1998 | Ahmed et al. | |
| 5,878,536 A | 3/1999 | Demmitt et al. | |
| 5,890,326 A | 4/1999 | Gallant et al. | |
| 5,911,661 A | 6/1999 | Murray et al. | |
| 5,966,760 A | 10/1999 | Gallant et al. | |
| 5,991,947 A | 11/1999 | Lavin et al. | |
| 6,006,379 A | 12/1999 | Hensley | |
| 6,096,025 A | 8/2000 | Borders | |
| 6,145,253 A | 11/2000 | Gallant et al. | |
| 6,213,481 B1 | 4/2001 | Marchese et al. | |
| 6,243,993 B1 | 6/2001 | Swensson | |
| 6,256,936 B1 | 7/2001 | Swensson et al. | |
| 6,325,097 B1 | 12/2001 | Gallant et al. | |
| 6,405,491 B1 | 6/2002 | Gallant | |
| 6,447,491 B1 * | 9/2002 | Lord | 604/319 |
| 6,591,437 B1 * | 7/2003 | Phillips | 5/713 |
| 2002/0066142 A1 * | 6/2002 | Osborne et al. | 5/600 |
| 2006/0258964 A1 * | 11/2006 | Biondo et al. | 601/152 |

FOREIGN PATENT DOCUMENTS

| | | |
|---|---|---|
| DE | 836236 | 4/1952 |
| DE | 1930789 | 12/1970 |
| DE | 2204573 | 8/1973 |
| DE | 2228898 | 1/1974 |
| DE | 2544221 | 12/1976 |
| DE | 8434471 | 5/1985 |
| DE | 3541017 | 6/1986 |
| DE | 9204321 | 5/1992 |
| DE | 4228873 | 10/1993 |
| DE | 4416618 | 7/1995 |
| DE | 4409069 | 9/1995 |
| DE | 29720195 | 1/1998 |
| DE | 19750478 | 6/1999 |
| DE | 29923051 | 4/2000 |
| DE | 200 18 317 U1 | 2/2001 |
| EP | 0 311 336 | 4/1989 |
| EP | 0 481 942 A1 | 4/1992 |
| EP | 0947187 | 10/1999 |
| EP | 0 966 944 A2 | 12/1999 |
| EP | 0 969 241 A1 | 1/2000 |
| EP | 1030143 | 8/2000 |
| FR | 2213070 | 8/1974 |
| GB | 1 490 381 | 11/1977 |
| WO | WO 94/20784 | 9/1994 |
| WO | WO 98/33419 | 8/1998 |
| WO | WO 98/50840 | 11/1998 |
| WO | WO 01/33529 | 5/2001 |
| WO | WO 01/37922 | 5/2001 |

OTHER PUBLICATIONS

Hill-Rom Company, Inc. Video 2 (Nov. 1999).

* cited by examiner

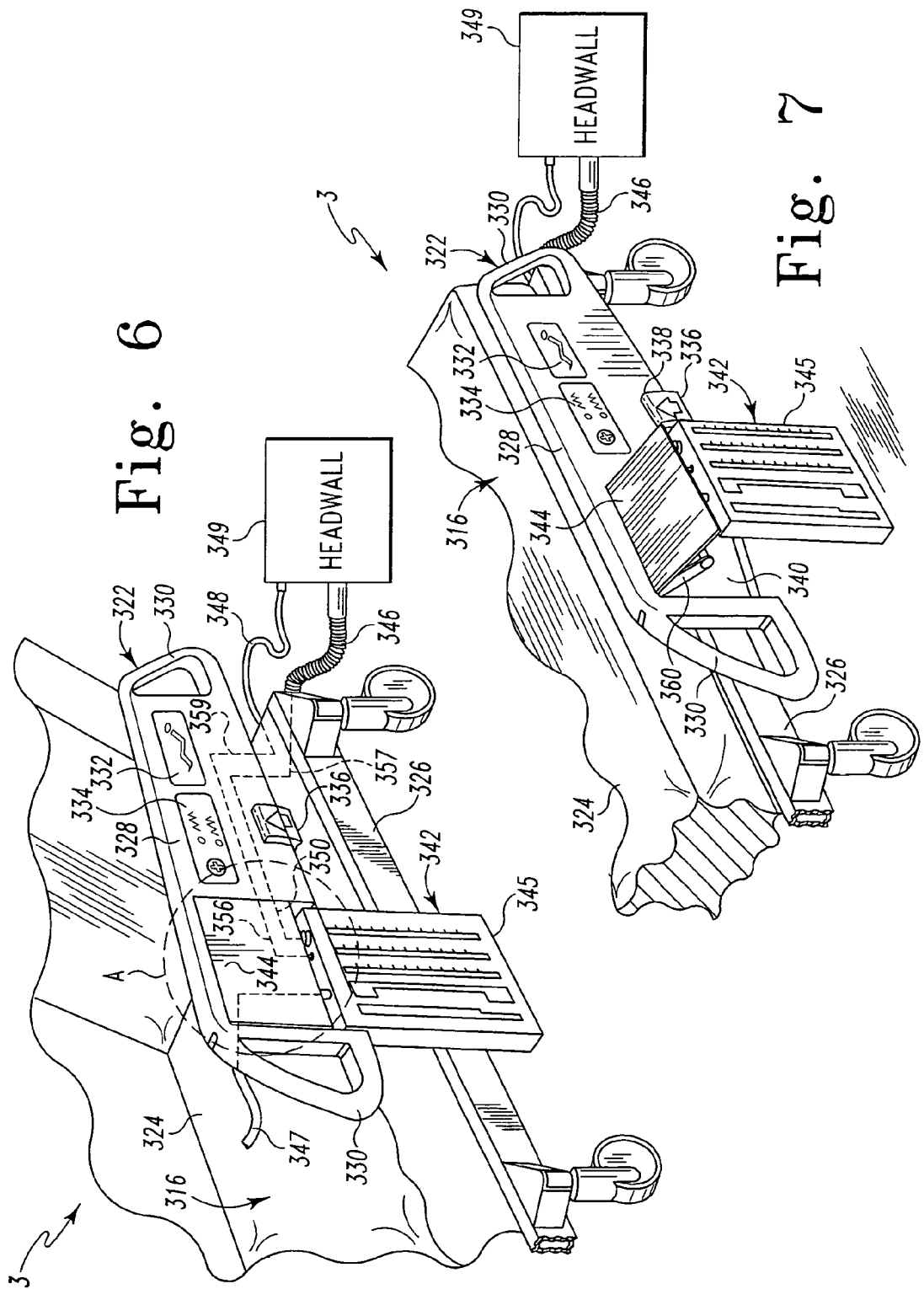

HOSPITAL BED SIDE RAIL WITH MEDICAL TREATMENT CONTROL UNIT

CROSS-REFERENCE TO RELATED APPLICATION

This application is a divisional application of U.S. Ser. No. 10/154,312, filed May 23, 2002, now U.S. Pat. No. 6,895,715 the disclosure of which is hereby incorporated by reference herein. U.S. Ser. No. 10/154,312 claims priority under 35 U.S.C. §119(e) to U.S. Provisional Application No. 60/293,949, filed May 25, 2001, which is expressly incorporated by reference herein.

TECHNICAL FIELD

The present disclosure relates to patient care apparatus for treating a patient in a healthcare facility. The patient care apparatus has, for example, a headwall to provide services to one or more of the patient, a bed for the patient, and other patient care equipment.

BACKGROUND AND SUMMARY

It is known to provide headwalls in rooms of healthcare facilities. A headwall is typically mounted next to one of the room walls and provides one or more services to, for example, a patient, a bed for the patient, and other patient care equipment.

According to the present disclosure, a headwall is adapted for use with a bed in a room of a healthcare facility. The headwall has a first service delivery unit having a first service connector to provide a first service to the bed. The headwall also has a second service delivery unit having a cavity and a second service connector to provide a second service to the bed. The second service delivery unit is to be supported by at least one of a wall of the room and the first service delivery unit for movement between a storage position in which the second service connector is positioned in the cavity and a use position in which the second service connector is positioned outside the cavity to allow the bed to dock to the second service delivery unit for transmission of the second service from the second service connector to the bed.

According to another aspect of the disclosure, the headwall has a support to be coupled to the wall and a service delivery unit. The service delivery unit has a service connector and is coupled to the support for pivotable movement of the service delivery unit between a storage position in which the service connector is to be positioned adjacent to the wall and a use position in which the service connector is positioned away from the first position to allow the bed to dock to the service delivery unit for transmission of a service from the service connector to the bed. The service connector is one of an electrical power outlet, a negative pressure port, a medical gas port, a hydraulic fluid port, and a motor.

According to another aspect of the disclosure, a headwall arrangement is adapted for use in a healthcare facility having a first room and a second room that share a common wall. The first room has a first bed therein and the second room has a second bed therein. The headwall arrangement a first headwall to be positioned in the first room to provide a first service to the first bed and a second headwall to be positioned in the second room to provide a second service to the second bed. The headwall arrangement has a bridging portion to be positioned in an opening in the common wall and the first headwall and the second headwall are coupled to the bridging portion.

According to another aspect of the disclosure, a patient care apparatus is adapted for use with a patient. The patient care apparatus has a bed to support the patient and the bed has a side rail. The patient care apparatus has patient care equipment having a medical treatment control unit and a medical treatment line coupled to the medical treatment control unit to provide medical treatment controlled by the medical treatment control unit to the patient. The medical treatment control unit is coupled to the side rail and positioned in a cavity of the side rail.

According to another aspect of the disclosure, the patient care apparatus has a chest drainage unit to drain material from a chest of the patient supported by the bed. The chest drainage unit is coupled to the side rail.

Additional features will become apparent to those skilled in the art upon consideration of the following detailed description of illustrative embodiments exemplifying the best mode as presently perceived.

BRIEF DESCRIPTION OF THE DRAWINGS

The detailed description particularly refers to the accompanying figures in which:

FIG. 6 is a perspective view of a portion of a hospital bed showing the hospital bed including a side rail, a chest drainage unit coupled to the side rail, an upper portion of the chest drainage unit being received in a lower portion of a cavity formed in the side rail, the side rail including a rectangular panel covering an upper portion of the cavity, and the hospital bed including a negative pressure line and a communication line extending from a base of the hospital bed and coupled to a headwall (shown diagrammatically);

FIG. 7 is a perspective view similar to FIG. 6 showing the side rail moved to a lowered position, a bottom surface of the chest drainage unit engaging a floor of the hospital room, and the rectangular panel pivoted laterally outwardly away from the side rail;

DETAILED DESCRIPTION OF THE DRAWINGS

Figure 1:
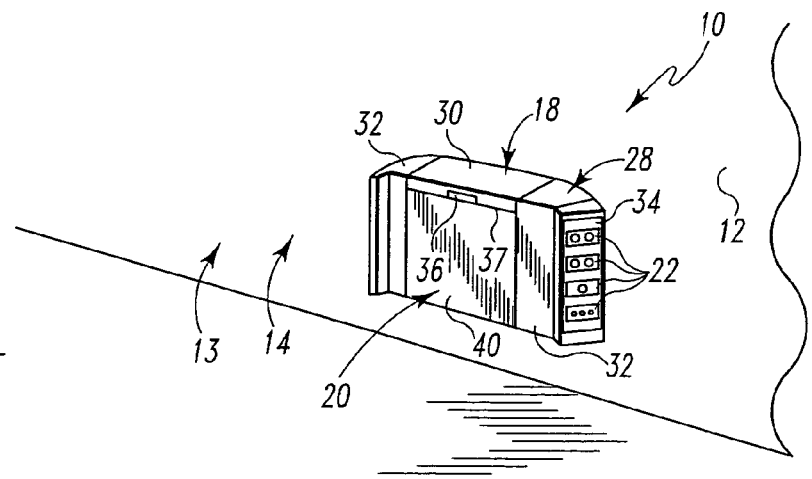
FIG. 1 is a perspective view of a headwall mounted to a wall of a hospital room showing the headwall including a downwardly facing C-shaped first service delivery unit having a pair of side portions and a top portion extending between the side portions and a second service delivery unit nested in a storage position between the side portions and the top portion, one of the side portions having a plurality of service connectors to provide a variety of services for transmission to a hospital bed.
Figure 2:
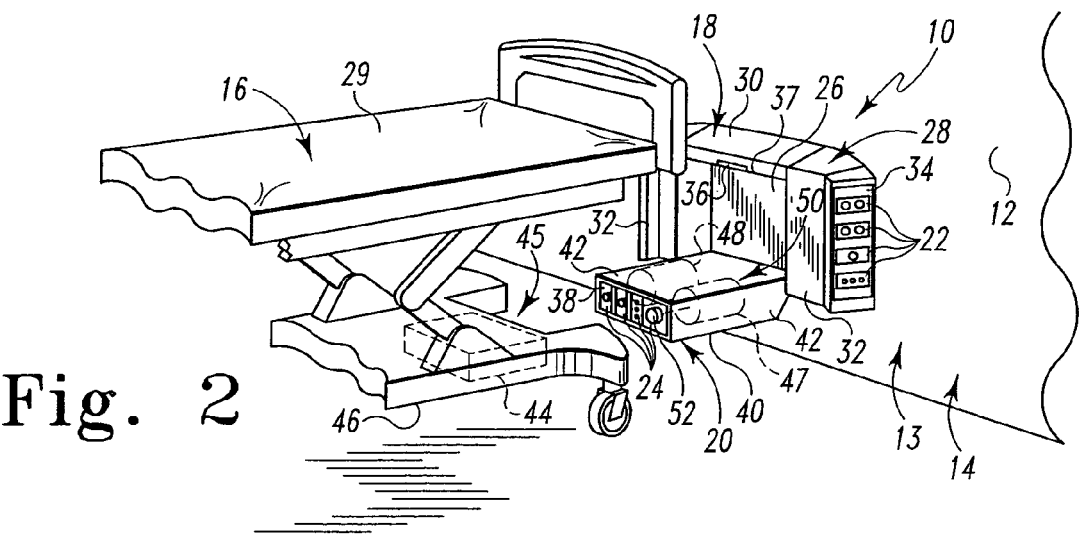
FIG. 2 is a perspective view similar to FIG. 1 showing the second service delivery unit pivoted relative to the first service delivery unit to a use position, the second service delivery unit having a plurality of service connectors, a hospital bed arranged for docking to the second service delivery unit for transmission of services from the service connectors of the second service delivery unit to the hospital bed.
Figure 3:
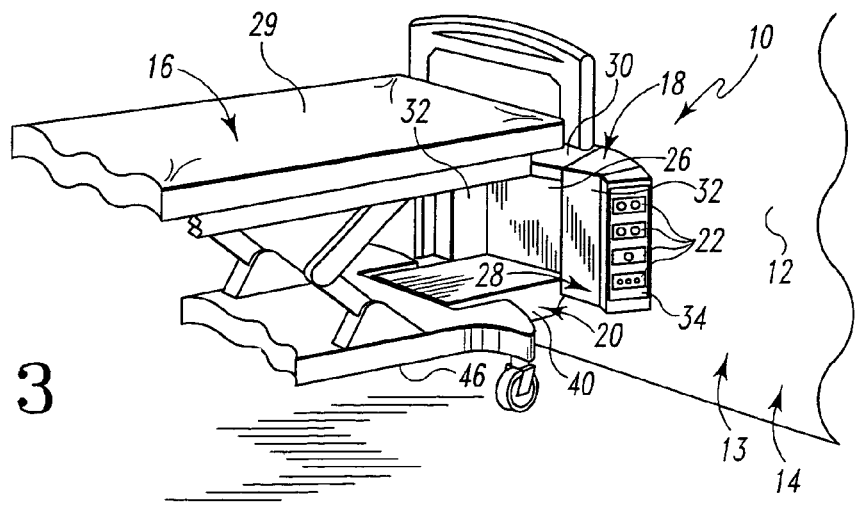
FIG. 3 is a perspective view similar to FIG. 2 showing the hospital bed docked to the second service delivery unity to receive services such as power, communications, air and negative pressure from the second service delivery unit and showing that the second service delivery unit is configured to properly position the bed relative to the headwall so that a patient support deck of the hospital bed remains spaced apart from the headwall to avoid contacting the headwall during raising and lowering of the deck.

A headwall 10 is mounted to a wall 12 of a room 13 of a healthcare facility 14 as shown in FIGS. 1-3. Headwall 10 provides a variety of services for transmission to a hospital bed 16 (see FIGS. 2-3) in room 13. Facility 14 is, for example, a hospital, a nursing facility, the home of a patient, or other location to care for a patient.

Headwall 10 has a first service delivery unit 18 and a second service delivery unit 20, as shown in FIGS. 1-3. Unit 18 has a housing 28 and a plurality of first service connectors 22 mounted thereto to provide services for transmission to bed 16. Unit 20 has a housing 40 and a plurality of second service connectors 24 mounted thereto for transmission of services to bed 16.

Service connectors 22, 24 are arranged to provide the variety of services for bed 16. Some of service connectors 22, 24 are electrical power outlets to provide electrical power to bed 16. Some of the service connectors 22, 24 are medical gas ports to provide medical gas, such as, for example, any one or more of oxygen, nitrogen, and air to bed 16. Some of the service connectors 22, 24 are negative pressure ports to provide negative pressure to bed 16. The negative pressure source (not shown) supplying the negative pressure for such negative pressure ports is, for example, the central negative pressure source of facility 14 or a pump mounted in one of units 118, 120, wall 112, or some other suitable location. Some of the service connectors 22, 24 are data communication ports to transmit data, such as, for example, any one or more of audio data, video data, and informational data, to bed 16. Service lines (not shown) that receive services from equipment located remotely from room 13 are routed through wall 12 to associated service connectors 22, 24.

Units 18, 20 are mounted in room 13. Housing 28 of unit 18 is mounted to wall 18 in a fixed position. Housing 40 of unit 20 is mounted to housing 28 for pivotable movement of unit 20 between a storage position (see FIG. 1) and a use position (see FIGS. 2-3). Housing 28 thus acts as a support for unit 20. In some embodiments, unit 20 is mounted to wall 12 in addition to or instead of unit 18. In the storage position, unit 20 nests in a cavity 26 formed in housing 28 and extends vertically alongside wall 12. In the use position, unit 20 extends horizontally away from wall 12 to allow bed 16 to dock to unit 20 to transmit services directly from unit 20 to bed 16. Service connectors 24, which are coupled to an end face 38 of housing 40, are positioned in cavity 26 in the storage position and outside cavity 26 in the use position. When bed 16 is docked to unit 20, unit 20 spaces a patient support deck 29 of bed 16 apart from unit 18 so that patient support deck 29 does not contact unit 18 during raising and lowering of patient support deck 29.

Housing 28 and housing 40 are configured so that housing 40 nests in housing 28 in the storage position, as shown in FIG. 1. Housing 28 has a horizontally extending top portion 30 and a pair of side portions 32 extending downwardly from top portion 30, as shown in FIGS. 1-3. Top and side portions 30, 32 cooperate to provide cavity 26 and to form a downwardly facing C-shape. Housing 40 has opposite side faces 42 and end face 38 which is positioned between side faces 42, as shown in FIGS. 2-3. In the storage position, each side face 42 is next to and faces one of side portions 32 and end face 38 is next to and faces top portion 30. Each side portion 32 has a face 34 to which some of the first service connectors 22 are coupled, as shown with respect to one of side portions 32 in FIGS. 1-3.

Top portion 30 has a central notch 36, as shown in FIGS. 1-2. Notch 36 is formed in a lower front edge 37 of top portion 30 to allow a caregiver access to an end face 38 of unit 20 to which second service connectors 24 are coupled so that the caregiver can pivot unit 20 between its storage and use positions.

In the use position, unit 20 is arranged to extend into a unit-receiving space 44 formed in a base 46 of bed 16, as shown in FIG. 3. When bed 16 is docked to unit 20, at least some of service connectors 24 are coupled to corresponding service connectors (not shown) of base 46 to provide services to bed 16.

In some embodiments, base 46 has a hydraulic pump and controller package 44 and unit 20 has an electric motor 47 and a hydraulic fluid reservoir 48 housed in an interior region 50 of housing 40, as shown in FIG. 2. The controller portion of package 44 is coupled to motor 47 to control operation of motor 47. Motor 47 has a shaft 52, which is one of the second service connectors 24, coupled to the hydraulic pump portion of package 44 to operate the hydraulic pump portion. The hydraulic pump portion is, in turn, coupled to hydraulic fluid reservoir 48 via one of the second service connectors 24 providing a hydraulic fluid port to pump hydraulic fluid to various hydraulic fluid cylinders (not shown) on-board bed 16 which control movement of various portions of bed 16. Such movement includes articulation of patient-support deck 29, tilting of patient-support deck 29 relative to base 46, and adjusting the elevation of patient-support deck 29 relative to base 46. Housing motor 47 and hydraulic fluid reservoir 48 on-board unit 18 makes bed 13 lighter in weight than if they were placed on-board bed 16 so that bed 13 is easier to transport about facility 14.

Figure 4:
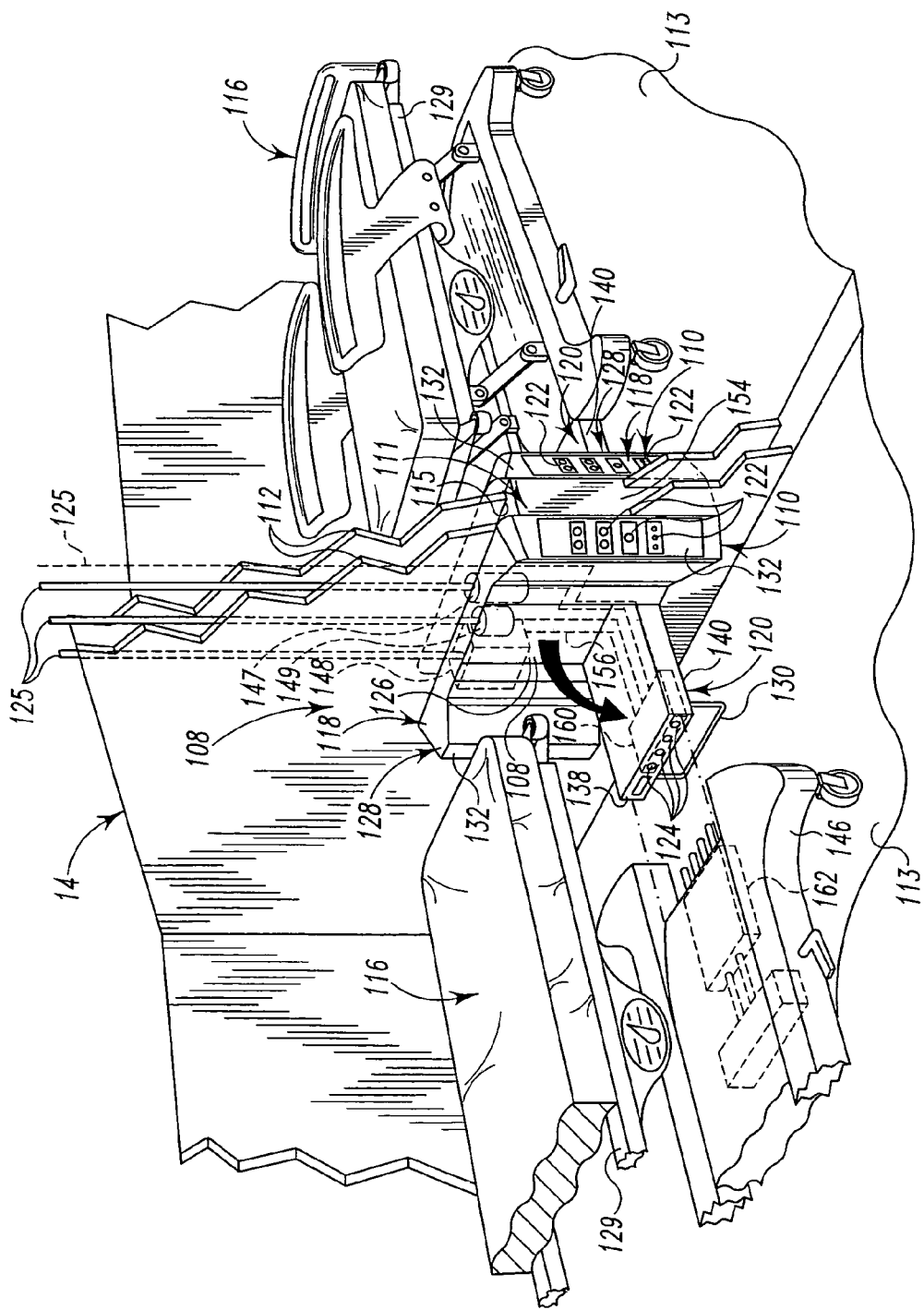
FIG. 4 is a perspective view of a back-to-back headwall arrangement showing a pair of head walls of the arrangement coupled together by a bridging portion located between the headwalls, a hospital room wall surrounding the bridging portion and each headwall being located in a respective hospital room on opposite sides of the hospital room wall, each headwall including a service delivery unit that is pivotable from a storage position nested between side portions of the respective headwall to a use position, a first hospital bed in the far hospital room being docked to the respective pivotable service delivery unit, and a second hospital bed in the near room being arranged for docking to the respective pivotable service delivery unit.

A back-to-back headwall arrangement 108 is configured to provide a variety of services to a pair of hospital beds 116 located in a pair of adjacent rooms 113 in facility 14, as shown in FIG. 4. Arrangement 108 has a pair of headwalls 110, one in each room 113, and a bridging portion 111 coupled to headwalls 110 and mounted therebetween in an opening 115 formed in a wall 112 common to both rooms 113 to provide services to headwalls 110. Headwalls 110 are thus located on opposite sides of wall 112 to provide services to beds 116.

Each headwall 110 has a first service delivery unit 118 and a second service delivery unit 120, as shown in FIG. 4. Unit 118 has a housing 128 and a plurality of first service connectors 122 mounted thereto to provide services for transmission to respective bed 116. Unit 120 has a housing 140 and a plurality of second service connectors 124 mounted thereto for transmission of services to respective bed 116.

Service connectors 122, 124 are arranged to provide the variety of services for respective bed 116. Some of service connectors 122, 124 are electrical power outlets to provide electrical power to respective bed 116. Some of the service connectors 122, 124 are medical gas ports to provide medical gas, such as, for example, any one or more of oxygen, nitrogen, and air to respective bed 116. Some of the service connectors 122, 124 are negative pressure ports to provide negative pressure to respective bed 116. The negative pressure source (not shown) supplying the negative pressure for such negative pressure ports is, for example, the central negative pressure source of facility 14 or a pump mounted in one of units 118, 120, wall 112, or some other suitable location. Some of the service connectors 122, 124 are data communication ports to transmit data, such as, for example, any one or more of audio data, video data, and informational data, to respective bed 116. Each bed 113 has a base 146 and a control package 162 contained in base 146 to interface with service connectors 124 of respective headwall 110.

With respect to each headwall 110, housing 128 is mounted to wall 18 in a fixed position and housing 140 is mounted to housing 128 for pivotable movement of unit 120 between a storage position and a use position (see FIG. 4). Housing 128 thus acts as a support for unit 120. In some embodiments, unit 120 is mounted to wall 112 and/or bridging portion 111 in addition to or instead of unit 118. In the storage position, unit 120 is oriented vertically and nests in a cavity 126 provided between side portions 132 of housing 128. In the use position, unit 120 extends horizontally to allow control package 162 contained in a base 146 of respective bed 16 to dock to unit 120 to transmit services directly from unit 120 to respective bed 116. Service connectors 124, which are coupled to an end face 138 of housing 140, are positioned in cavity 126 in the storage position and outside cavity 126 in the use position. When respective bed 116 is docked to unit 120, unit 120 spaces a patient support deck 129 of respective bed 116 apart from unit 118 so that patient support deck 129 does not contact unit 118 during raising and lowering of patient support deck 129.

A floor-engaging support or bail 130 is coupled to each housing 140, as shown in FIG. 4. When bail 130 engages the floor of respective room 113, respective unit 120 is oriented in its use position.

Bridging portion 111 has a housing 154 coupled to and positioned between housings 128, 140 and wall 112, as shown in FIG. 4. Housing 154 provides interior region 156 and has service delivery equipment 158 positioned in interior region 156. Equipment 158 includes service lines 125 that receive services from equipment (not shown) located remotely from rooms 113 and are routed through wall 112 and interior region 156 to associated service connectors 122, 124 of headwalls 110.

In some embodiments, equipment 158 includes an electric motor 147, a hydraulic fluid reservoir 148, and a pump 149, as shown in FIG. 4. Motor 147, reservoir 148, and pump 149 are housed in interior region 156 and cooperate to provide hydraulic fluid to each bed 116 via respective headwall 110. Motor 147 is coupled to pump 149 to operate pump 149. Pump 149 is coupled to reservoir 148 and a valve pack 160 of each headwall 110 to pump hydraulic fluid from reservoir 148 to each valve pack 160. Each valve pack 160 has one or more valves to open and close certain service connectors 124 to open and close corresponding hydraulic fluid flow paths to respective bed 113. By housing motor 147, reservoir 148, and pump 149 in bridging portion 111, neither of beds 113 needs to carry these components thereby reducing the weight of beds 113 and making beds 113 easier to transport about facility 14.

Figure 5:
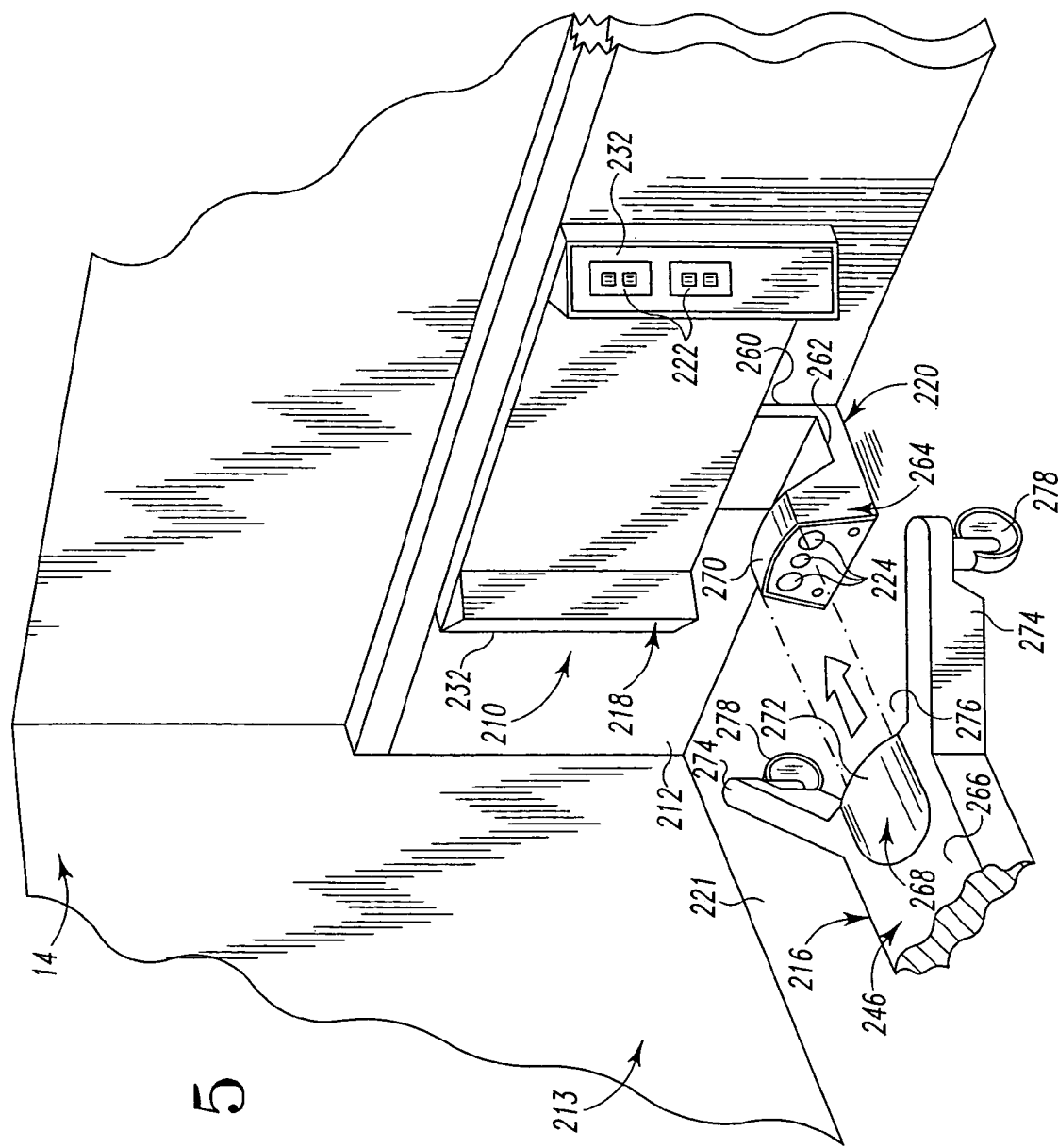
FIG. 5 is a perspective view of a headwall having a wall-mounted unit mounted to a hospital room wall and a floor-mounted unit mounted to a hospital room floor, each of the wall-mounted unit and the floor-mounted unit having a plurality of service connectors to provide a variety of services to a hospital bed arranged for docking to the floor-mounted unit.

A headwall 210, shown in FIG. 5, is configured to couple to a base 246 of a hospital bed 216 located in a room 213 of facility 14 to provide services to bed 216. Headwall 210 has a wall-mounted unit 218 mounted to a wall 212 of room 213 and a floor-mounted unit 220 mounted to a floor 221 of room 213.

Unit 218 has a pair of side portions 232. Portions 232 have a plurality of first service connectors 222 which are, for example, electrical power outlets to provide electrical power.

Unit 220 extends away from wall 212 along floor 221 to interface directly with base 246. Unit 220 has a vertical portion 260 extending vertically between an undersurface of unit 218 and floor 221 and has a horizontal portion 262 extending horizontally away from portion 260 along floor 221. Unit 220 further has an interface portion 264 extending upwardly from horizontal portion 262 in spaced apart relation with portion 260.

Interface portion 264 includes second service connectors 224 that mate automatically with corresponding service connectors (not shown) included in base 246 when base 246 is docked to interface portion 264. Illustratively, at least one of connectors 224 provides electrical power to run equipment (not shown) included in bed 216. Other connectors 224 are configured for communication and data transmission between associated equipment on bed 216 and equipment (not shown) located remotely from the bed 216. Each of portions 260, 262, 264 has interior regions through which lines are routed to respective connectors 224. Optionally, interface portion 264 includes additional service connectors configured to provide medical gas, such as any one or more of oxygen, nitrogen, air, and other gases, and negative pressure to bed 216. Base 246 and interface portion 264 cooperate so that the service connectors of base 246 connect quickly and easily to service connectors 224 when base 246 is docked to interface portion 264 thereby eliminating the need to handle various power cords, gas lines, data lines, and communication lines.

Base 246 includes a main, central portion 266 formed to include a domed portion 268 at an end thereof. Interface portion 264 has an upper surface 270 that matches the contour of an upper surface 272 of domed portion 268 so that upper surfaces 270, 272 form a substantially continuous surface when bed 216 is docked to interface portion 264. Base 246 further includes arm portions 274 that extend toward wall 212 and laterally outwardly away from corner regions of central portion 266 to define a docking space 276 therebetween. Unit 220 extends into docking space 276 when base 246 is docked to interface portion 264. Base 192 further includes casters 278 to engage floor 221. Two of casters 278 are mounted to respective distal ends of arm portions 274.

Figure 8:
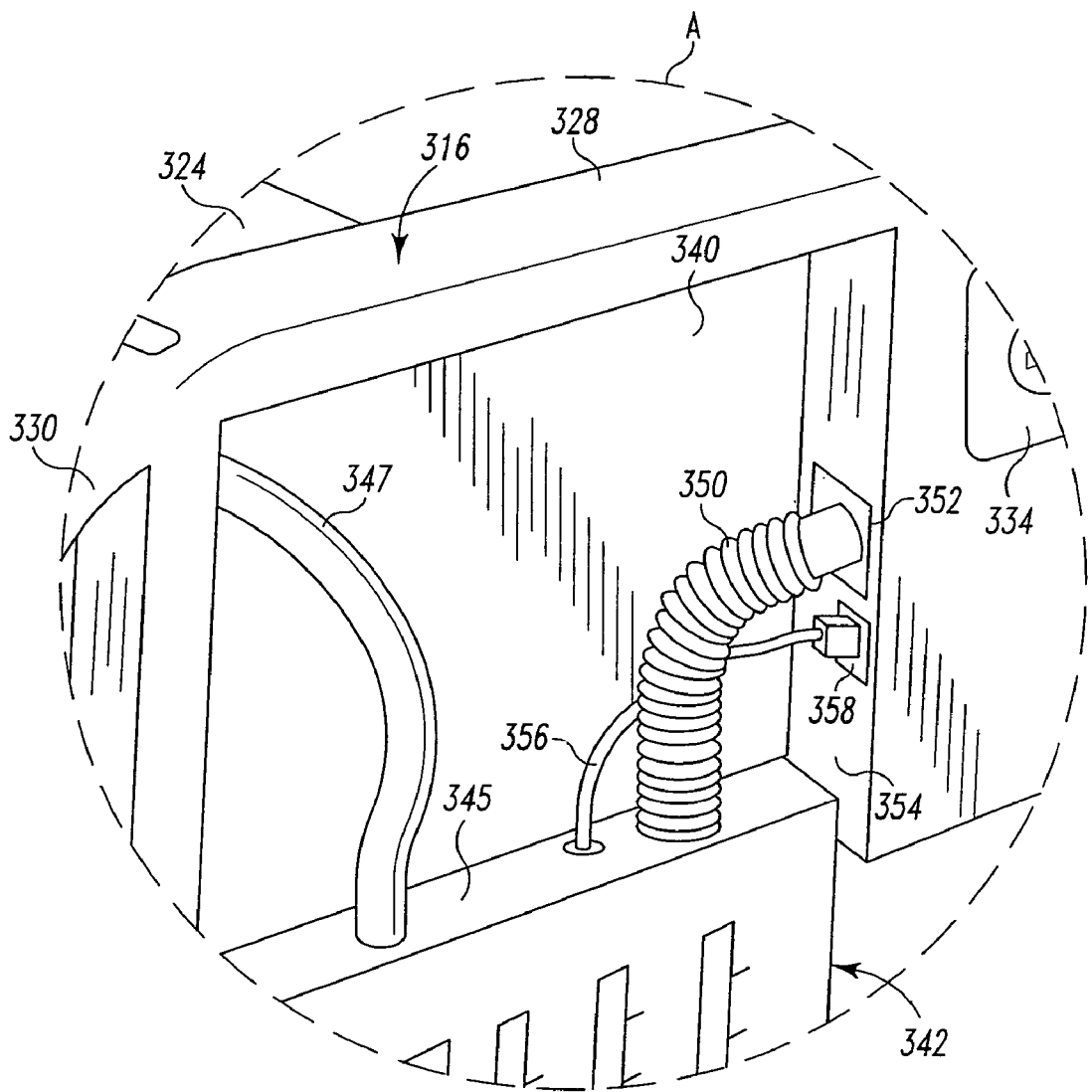
FIG. 8 is an enlarged perspective view of a portion of the side rail of FIG. 6 with the rectangular plate removed showing from left to right a drainage line extending between a top of the chest drainage unit and a vertical left side wall of the cavity of the side rail to drain material from the chest of a patient (not shown) on the hospital bed, a communication line extending between the top of the chest drainage unit and a communication port situated along a vertical right side wall of the cavity, and a negative pressure line extending between the top of the chest drainage unit and a negative pressure port situated along the vertical right side wall.

A patient care apparatus 309 is shown in FIGS. 6-8. Apparatus 309 has a hospital bed 316 and patient care equipment such as a chest drainage unit 342 (e.g., a Pleur Evac® chest drainage unit) integrated into bed 316 and configured to drain material from the chest of a patient supported by bed 316.

Hospital bed 316 includes a mattress 324, a deck (not shown) supporting mattress 324, a base 326, and a lift assembly (not shown) coupled to base 326 and to the deck. Bed 316 further includes a side rail assembly 322 coupled to the deck for movement between a raised position, shown in FIG. 6, and a lowered position, shown in FIG. 8. Side rail assembly 322 includes a longitudinally extending main portion 328 and a pair of handle portions 330 appended to main portion 328 at opposite ends thereof. Handle portions 330 are gripped by caregivers to maneuver hospital bed 316 during transport through a hospital. Handle portions 330 are also gripped by caregivers during raising and lowering of side rail assembly 322. Side rail assembly 322 further includes a first control panel 332 coupled to a laterally outwardly facing vertical surface of main portion 328, a second control panel 334 coupled to the laterally outwardly facing vertical surface of main portion 328, and a release handle 336 positioned to lie in a handle-receiving notch 338 formed in the bottom edge of main portion 328.

When side rail assembly 322 is in the raised position, movement of release handle 336 to an unlocking position releases a locking mechanism (not shown) of side rail assembly 322 allowing side rail assembly 322 to lower automatically from the raised position to the lowered position. First control panel 332 includes a plurality of inputs that are engaged by a caregiver to control various drive mechanisms (not shown) that raise, lower, tilt, and articulate the deck of hospital bed 316. A third control panel (not shown) that is substantially similar to control panel 332 is coupled to an inwardly facing surface of main portion 328 and is used by a patient to raise, lower, tilt, and articulate the deck of hospital bed 316. Second control panel 334 is dedicated to the control of chest drainage unit 342 which is mounted to side rail assembly 322. In some embodiments, second control panel 334 is dedicated to the control of other specialized patient care equipment integrated into hospital bed 316, such as, for example, infusion units, vacuum bandage units, or any other patient care equipment including patient-monitoring equipment, patient-temperature regulation equipment, and waste-management equipment.

Main portion 328 of side rail assembly 322 is formed to include a cavity 340, shown in FIGS. 7 and 8, that is open along the bottom edge of main portion 328 and that is open at the outwardly facing vertical surface of main portion 328. A medical treatment control unit 345 of chest drainage unit 342 is configured to control drainage of material from the chest of a patient on mattress 324 and is coupled to side rail assembly 322 such that, when side rail assembly 322 is in the raised position, an upper portion of control unit 345 is received in a lower portion of cavity 340 as shown in FIG. 6. Side rail assembly 322 includes a rectangular panel 344 covering the portion of cavity 340 occupying the space above the top surface of control unit 345. Illustrative cavity 340 is substantially rectangular in shape as is the housing of the control unit 345. However, cavity 340 can have shapes other than rectangular as dictated by the shape of the specialized patient care equipment to be integrated into bed 316.

Chest drainage unit 342 has a medical treatment or chest drainage line 347, as shown in FIGS. 6 and 8. Line 347 is coupled to control unit 345 and extends through side rail assembly 322 to a patient support region of mattress 324 to drain material from the chest of the patient supported on mattress 324 to control unit 345.

As shown in FIGS. 6 and 7, an external negative pressure (i.e., pressure below atmospheric pressure) line 346 and an external communication line 348 extend from base 326 of hospital bed 316 and are configured to connect to service connectors of a headwall 349. In alternative embodiments, base 326 of bed 316 is configured like base 246, shown in FIG. 5, and like base 46 of bed 16, shown in FIGS. 2 and 3, so as to be able to dock to respective units 20, 220 of headwalls 10, 220, thereby allowing for the elimination of lines 346, 348. In such alternative embodiments, bed 316 receives negative pressure from, and exchanges communication data with, the respective unit 20, 220.

Side rail assembly 322 includes an internal negative pressure line 350 extending between the top surface of control unit 345 and a negative pressure port 352 situated along a vertical cavity side wall 354 as shown in FIG. 8. Side rail assembly 322 further includes a communication line 356 extending between the top of control unit 345 and a communication port 358 situated along vertical cavity side wall 354 beneath negative pressure port 352 as also shown in FIG. 8. Bed 316 includes additional negative pressure lines 357 and communication lines 359 that interconnect lines 346, 348 with lines 350, 356, respectively. By integrating chest drainage unit 342 into side rail assembly 322 of bed 316, many of the negative pressure lines and communication lines associated with chest drainage unit 342 are hidden and out of the way, thereby reducing the amount of clutter around bed 316 and minimizing the chance that the chest drainage lines will become entangled with lines or tubes associated with other patient care equipment.

A majority of control unit 345 extends downwardly out of cavity 340 when side rail assembly 322 is in the raised position as shown in FIG. 6. Depending upon the elevation of deck of bed 316 relative to base 326, as governed by the position of the lift assembly of bed 316, a bottom surface of control unit 345 may come into contact with the floor during movement of side rail assembly 322 from the raised position to the lowered position. However, side rail assembly 322 includes a bail or linkage 360 coupled to main portion 328 within cavity 340 and coupled to an upper end of control unit 345. Linkage 360 is configured to maintain control unit 342 in a substantially upright orientation during movement of side rail assembly 322 between the raised and lowered positions even if the bottom surface of control unit 345 contacts the floor when side rail assembly 322 is at any intermediate position between the raised and lowered positions. Panel 344 is pivotably coupled at its upper end to main portion 328 of side rail assembly 322 and linkage 360 causes panel 344 to pivot laterally outwardly away from main portion 328 after the bottom surface of control unit 345 contacts the floor as shown, for example, in FIG. 7.

Figure 9:
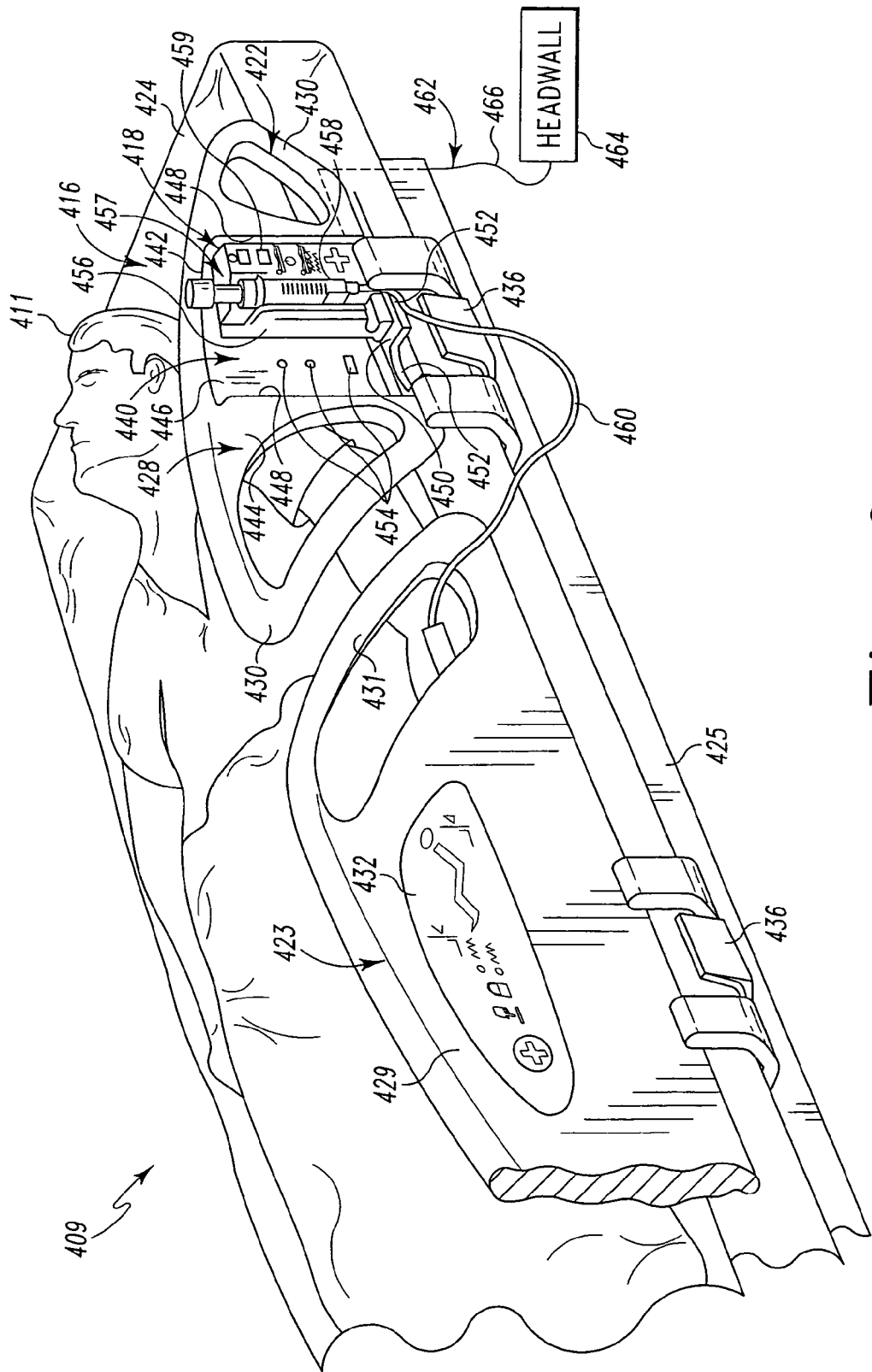
FIG. 9 is a perspective view of a portion of a hospital bed showing a head end side rail of the hospital bed having a cavity formed therein, an infusion unit received in the cavity to provide medication to a patient lying on the bed, and an electrical power line extending through the bed to a headwall to provide electrical power to the infusion unit.

A patient care apparatus 409 is shown in FIG. 9. Apparatus 409 has a hospital bed 416 and patient care equipment such as an infusion unit 418 integrated into bed 416 and configured to provide medication to a patient 411 supported by bed 416.

Bed 416 includes a mattress 424, a deck 425 supporting mattress 424, a first or head-end side rail assembly 422 coupled to deck 425, and a second or foot-end side rail assembly 423 coupled to deck 425 as shown in FIG. 9. Side rail assembly 423 is spaced apart from but is longitudinally aligned with side rail assembly 422. Side rail assembly 422 includes a main portion 428 and a pair of handle portions 430 coupled to opposite ends of main portion 428. Handle portions 430 are gripped by caregivers to maneuver hospital bed 416 during transport of bed 416 through a hospital. Handle portions 430 are also gripped by caregivers during raising and lowering of side rail assembly 422.

Side rail assembly 423 includes a main portion 429 to which one or more control panels 432 are coupled and side rail assembly 423 also includes one or more handle portions 431. Each of side rail assemblies 422, 423 includes a respective release handle 436 that is actuated to unlock corresponding side rail assemblies 422, 423 for movement from respective raised positions, shown in FIG. 9, to respective lowered positions (not shown).

Main portion 428 of side rail assembly 422 is formed to include a cavity 440 that is sized to receive various pieces of patient care equipment therein. For example, illustrative cavity 440 is sized to receive a pair of infusion units 418 (only one of which is shown in FIG. 9). Cavity 440 is open at an upper edge 442 of main portion 428 and is open at the outwardly facing vertical surface 444 of main portion 428. Thus, cavity 440 is bounded by a vertical back wall surface 446 that extends parallel with the longitudinal dimension of bed 416 and by a pair of vertical side wall surfaces 448 that extend parallel with the transverse dimension of bed 416. Main portion 428 of side rail assembly 422 includes a ledge 450 that underlies cavity 440 and that extends along the bottom of main portion 428. Ledge 450 includes a pair of notches 452.

One or more couplers 454 either are mounted to or are formed in back wall surface 446 as shown in FIG. 9. Infusion unit 418 includes a housing 456 having couplers (not shown) that mate with couplers 454 to mount infusion unit 418 to side rail assembly 422. Couplers 454 may include, for example, headed pins or bolts and the couplers of infusion units 418 may include key hole slots that receive the headed pins or bolts. According to this disclosure, couplers 454 and the couplers on unit 418 may include many other types of structures, such as latches received in apertures, hooks that catch on pins or eyes, straps that capture units 418, clamps or grippers that clamp onto protrusions, magnets, and plugs or barbs received in receptacles.

Illustrative infusion unit 418 includes a control unit 457 configured to control delivery of medication to patient 411. Control unit 457 includes housing 456, a vertically oriented, cylindrical medication container 458, such as a syringe, coupled to housing 456, and a controller 459 to control discharge of medication from container 458. Infusion unit 418 operates in a known manner to deliver medication from container 458 to patient 411 on bed 416 through an infusion line 460. A bottom surface of housing 456 rests upon ledge 450 and line 460 extends downwardly from container 458 through one of notches 452. Housing 456 is sized to fit into cavity 440 so that no portion of housing 456 extends out of cavity 440. In addition, cavity 440 is sized so that two infusion units 418 are able to fit therein in side-by-side relation. It is within the scope of this disclosure for other types of patient care equipment having housings that extend out of cavity 440 to be mounted to main portion 428 of side rail assembly 422.

As shown in FIG. 9, an electrical power line 462 is routed from infusion unit 418 through bed 416 to a service connector of a headwall 464 to provide electrical power to infusion unit 418. In alternative embodiments, bed 416 has a base (not shown) configured like base 46 of bed 16, shown in FIGS. 2 and 3, and like base 246 of bed 216, shown in FIG. 5, so as to be able to dock to respective units 20, 220 of headwalls 10, 220, thereby allowing for the elimination of the portion 466 of line 462 that is external to bed 416.

Figure 10:
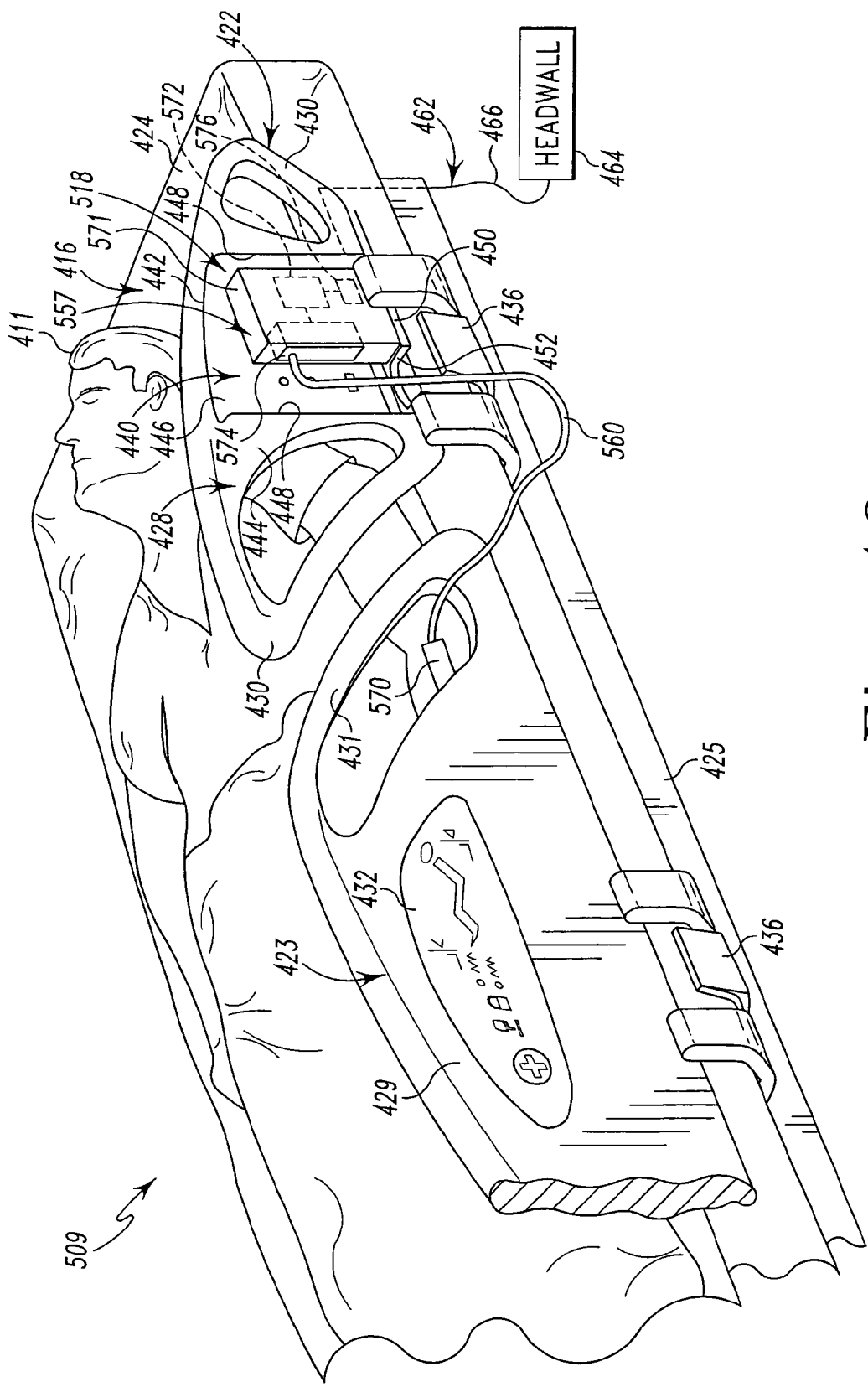
FIG. 10 is a perspective view of a portion of a hospital bed showing a head end side rail of the hospital bed having a cavity formed therein, a vacuum bandage unit received in the cavity to provide vacuum therapy to a wound of a patient lying on the bed, and an electrical power line extending through the bed to a headwall to provide electrical power to the vacuum bandage unit.

A patient care apparatus 509 is shown in FIG. 10. Some of the components of apparatus 509 are similar to components of apparatus 409 so that like reference numerals denote like components. Apparatus 509 has a vacuum bandage unit 518 (in place of infusion unit 418) integrated into bed 418 and configured to provide vacuum therapy to a wound of patient 411. A vacuum bandage unit suitable for use with apparatus 509 is disclosed in International Publication Number WO 01/37922 A2, published May 31, 2001, the disclosure of which is hereby incorporated by reference herein.

Vacuum bandage unit 518 has a control unit 557 to control the vacuum therapy provided to the wound of patient 411, a vacuum wound bandage 570 associated with the wound, and a negative pressure line 560 extending from control unit 557 to bandage 570 to provide negative pressure controlled and supplied by control unit 557 to bandage 570. Control unit 557 has a housing 571 mounted to surface 444 and resting on ledge 450 in cavity 440. Control unit 557 further has a waste collection canister 574 mounted in a receptacle formed in housing 571, a negative pressure source 572 in communication with canister 574, and a controller 576 to control negative pressure source 572. Negative pressure line 560 is coupled to canister 574 to provide negative pressure from negative pressure source 572 to bandage 570 so that waste material from bandage 570 can be suctioned into canister 573 for collection therein.

As shown in FIG. 10, an electrical power line 462 is routed from control unit 557 through bed 416 to a service connector of a headwall 464 to provide electrical power to control unit 557. In alternative embodiments, bed 416 has a base (not shown) configured like base 46 of bed 16, shown in FIGS. 2 and 3, and like base 246 of bed 216, shown in FIG. 5, so as to be able to dock to respective units 20, 220 of headwalls 10, 220, thereby allowing for the elimination of the portion 466 of line 462 that is external to bed 416. In other alternative embodiments, rather than being contained in housing 571, the source of negative pressure for bandage 570 is located remotely away from the room in which bed 416 is located and there is a negative pressure line (not shown) leading from control unit 557 through bed 416 to headwall 464 to access that negative pressure source. Such a remotely located negative pressure source is, for example, a hospital central negative pressure source that provides negative pressure for other hospital rooms as well.

Although certain illustrative embodiments have been disclosed in detail, variations and modifications exist within the scope and spirit of the disclosure as described and defined in the following claims.

What is claimed is:

1. A patient care apparatus adapted for use with a patient, the patient care apparatus comprising
a bed to support the patient, the bed having a side rail, and the side rail having a cavity formed within the side rail, a first aperture opening into the cavity and positioned to lie in a first substantially vertical plane, and a second aperture opening into the cavity and positioned to lie in a second substantially horizontal plane arranged to intersect the first substantially vertical plane at about a right angle, and
patient care equipment having a medical treatment control unit and a medical treatment line coupled to the medical treatment control unit to provide medical treatment controlled by the medical treatment control unit to the patient, the medical treatment control unit being movable between a first position wherein the medical treatment control unit is coupled to the side rail and positioned in the cavity and a second position wherein the medical treatment control unit is coupled to the side rail and positioned in spaced-apart relation to the cavity, wherein a front face of the medical treatment control unit faces outwardly in a use configuration when the medical treatment control unit is in both the first and second positions.

2. The patient care apparatus of claim 1, wherein the patient care equipment is a chest drainage unit to drain material from a chest of the patient, and the chest drainage unit has the medical treatment control unit to control drainage of the material from the chest of the patient and the medical treatment line to drain the material from the chest of the patient to the medical treatment control unit.

3. The patient care apparatus of claim 1, further comprising a headwall coupled to the bed, and the bed has a line extending from the headwall through the bed to the medical treatment control unit.

4. The patient care apparatus of claim 3, wherein the line is an electrical power line.

5. The patient care apparatus of claim 3, wherein the line is a data communication line.

6. A patient care apparatus adapted for use with a patient, the patient care apparatus comprising
a bed to support the patient, the bed having a side rail, and
a chest drainage unit to drain material from a chest of the patient supported by the bed, the chest drainage unit being coupled to the side rail,
wherein the chest drainage unit has a control unit to control drainage of the material from the chest of the patient,
wherein the side rail has (i) a negative pressure port coupled to the wall, (ii) a data communication port coupled to the wall, (iii) a negative pressure line coupled to the negative pressure port and the control unit to provide negative pressure to the control unit, and (iv) a data communication line coupled to the data communication port and the control unit.

7. The patient care apparatus of claim 6, wherein the control unit is coupled to the side rail for movement of the control unit relative to the side rail when the side rail is moved between raised and lowered positions.

8. The patient care apparatus of claim 7, wherein the control unit extends into the cavity when the side rail is positioned in its raised position and is positioned outside the cavity when the side rail is positioned in its lowered position.

9. A patient care apparatus adapted for use with a patient, the patient care apparatus comprising
a bed to support the patient, the bed having a side rail, and
a chest drainage unit to drain material from a chest of the patient supported by the bed, the chest drainage unit being coupled to the side rail,
wherein the chest drainage unit has a control unit to control drainage of the material from the chest of the patient,
wherein the side rail has (i) a negative pressure port coupled to the wall, (ii) a data communication port coupled to the wall, (iii) a negative pressure line coupled to the negative pressure port and the control unit to provide negative pressure to the control unit, and (iv) a data communication line coupled to the data communication port and the control unit,
wherein the control unit is coupled to the side rail for movement of the control unit relative to the side rail when the side rail is moved between raised and lowered positions,
wherein the control unit extends into the cavity when the side rail is positioned in its raised position and is positioned outside the cavity when the side rail is positioned in its lowered position, and
wherein the chest drainage unit has a linkage coupled to the side rail and the control unit to maintain the control unit in an upright orientation during movement of the control unit into and out of the cavity.

10. The patient care apparatus of claim 6, wherein the side rail has a negative pressure port and a negative pressure line coupled to the negative pressure port and the chest drainage unit to provide negative pressure to the chest drainage unit.

11. The patient care apparatus of claim 6, wherein the side rail has a data communication port and a data communication line coupled to the data communication port and the chest drainage unit.

12. The patient care apparatus of claim 1, wherein the patient care equipment includes a linkage coupled to the side rail and the medical treatment control unit to maintain the medical treatment control unit in an upright orientation during movement of the medical treatment control unit into and out of the cavity.

13. The patient care apparatus of claim 1, wherein the medical treatment control unit is positioned laterally-outwardly away from the cavity when the medical treatment control unit is in the second position such that top and bottom ends of the medical treatment control unit are positioned outside the cavity.

14. The patient care apparatus of claim 13, wherein the patient care equipment includes a panel pivotably coupled at its upper end to the side rail and pivotably coupled at its lower end to the medical treatment control unit.

15. The patient care apparatus of claim 1, wherein the line is a non-electrical line.

* * * * *